United States Patent [19]

Hirai et al.

[11] Patent Number: 4,842,829
[45] Date of Patent: Jun. 27, 1989

[54] DEODORIZING APPARATUS

[75] Inventors: Yoichi Hirai, Ohbu; Toshikazu Ito, Nagoya, both of Japan

[73] Assignee: Tohkai Kogyo Co., Ltd., Aichi, Japan

[21] Appl. No.: 931,392

[22] Filed: Nov. 14, 1986

[30] Foreign Application Priority Data

Nov. 19, 1985 [JP] Japan .................................. 60-259108
Jan. 13, 1986 [JP] Japan .................................... 61-4768

[51] Int. Cl.⁴ ............................................. B01J 19/08
[52] U.S. Cl. .............................. 422/186.08; 422/120; 422/186.07; 422/186.3; 422/5; 422/22; 422/24; 422/28; 250/435
[58] Field of Search ...................... 422/186.07, 186.08, 422/186.3, 186.1, 5, 22, 24, 28, 120, 123; 204/176; 250/435, 431

[56] References Cited

U.S. PATENT DOCUMENTS

| 1,981,650 | 11/1934 | Larsen | 422/123 |
| 3,745,750 | 7/1973 | Arff | 422/24 |
| 3,757,495 | 9/1973 | Sievers | 422/120 |
| 3,844,741 | 10/1974 | Dimitrik | 422/186.3 |
| 3,937,967 | 2/1976 | Steinitz | 250/435 |
| 4,630,530 | 12/1986 | Eckstrom et al. | 422/186.1 X |
| 4,694,179 | 9/1987 | Lew et al. | 422/186.3 |

FOREIGN PATENT DOCUMENTS

| 2207807 | 7/1973 | Fed. Rep. of Germany | 422/24 |
| 3101618 | 11/1982 | Fed. Rep. of Germany | 422/186.08 |
| 0062802 | 5/1980 | Japan | 422/123 |
| 0145045 | 8/1984 | Japan | 422/120 |

Primary Examiner—John F. Terapane
Assistant Examiner—Susan Wolffe
Attorney, Agent, or Firm—Dann, Dorfman, Herrell & Skillman

[57] ABSTRACT

A deodorizing apparatus adapted to be placed in an enclosure to deodorize the bad smelling components of the foul air within the enclosure. The body has an interior free space and a ozone-decomposing layer. Ozone is generated within the free space and flows in contact with the layer so that it is decomposed before it can leave the body. The ozone is formed either by silent (corona) discharge or by ultraviolet radiation in the free space, and the energy supplied is sufficient to cause the ozone to flow outwardly into contact with the layer and to draw in foul air through the layer so that the decomposing ozone effectively deodorizes by oxidation the bad smelling components. The flow through the device is sufficient to deodorize the entire enclosure.

15 Claims, 8 Drawing Sheets

DEODORIZING APPARATUS

FIELD OF THE INVENTION

The present invention relates to a simplified deodorizing apparatus using ozone which is applicable in the field of general home use.

BACKGROUND OF THE INVENTION

Recently, deodorization using ozone has been highlighted. In such a deodorizing apparatus, there have been such disadvantages that not only does the apparatus requires an ozonizer, a reaction chamber, surplus ozone decomposing equipment, and so on, so that the apparatus is large in size and high in cost, but it is necessary to use an ozone-resistant material in the ozone flow path because a high concentration of ozone is used. Therefore, such a deodorizing apparatus as described above has been utilized only for industrial use. The deodorizing effect due to ozone is, however, remarkable, and therefore it is considered that a field of utilization of the deodorizing apparatus other than that described above should be found. Development of a deodorizing apparatus which is reduced in size and simplified in arrangement so that it may be utilized for general home use has been earnestly desired.

SUMMARY OF THE INVENTION

An object of the invention is to provide a deodorizing apparatus using ozone which is reduced in size and simplified in arrangement so that it may be utilized for general home use to thereby expand the field of utilization of the deodorizing apparatus.

The deodorizing apparatus according to a first embodiment of the present invention comprises electric field energy means for generating ozone in a deodorizer body, the deodorizer body being constituted either by a layer of deodorizing material alone, or by the deodorizing material and an electrically insulating gas-impermeable member, the layer providing a flow path in which the ozone is in contact with the layer. The layer also serves as a support for adding a catalyzer for decomposing ozone. The deodorizing layer may comprise a porous filter with communicating pores owing to a three-dimensional skeleton structure. The deodorizer body has an interior free space portion for accommodating an electric field, an electric-field energy means being accommodated in or adjacent the free space portion such that the electric-field energy means can be energized so that the electric field generates ozone in the free space.

Ozone generated by the electric field in the free space portion of the deodorizing apparatus is caused to flow in contact with the deodorizing material by thermal and kinetic energy obtained from the electric field as it is subject to a decomposition reaction and is diffused outside in the form of oxygen. The apparatus provides sufficiently small flow resistance to permit said flow. Bad-smelling air in the outside is drawn into the free space portion so that it is in contact with the deodorizing material and replaces the diffused ozone as this diffusion progresses, and bad-smelling components of the air are subject to oxidation decomposition so as to be deodorized when contacted by ozone passing from this space portion in contact with the deodorizing material and diffused outside. The diffusion and drawing-in operation are performed in this manner so that the air in a sealed-up space surrounding the deodorizing apparatus is circulated for a long time to effect deodorization.

The deodorizing apparatus according to a second embodiment of the present invention comprises an ultraviolet-ray lamp for radiating ultraviolet rays of short wavelengths to generate ozone in a deodorizer body, the deodorizer body being constituted by either a deodorizing layer alone or the deodorizing layer and an electrically insulating gas-impermeable member, the layer serving as a support for adding a catalyzer for decomposing ozone. The deodorizer body has an free space portion formed in the inside thereof for accommodating the ultraviolet-ray lamp, or at least the luminous tube portion of the ultraviolet-ray lamp, the free space portion of the deodorizer body being closed into integral form after at least the luminous tube portion of the ultraviolet-ray lamp is accommodated in or near the free space portion in position such that the luminous tube portion can generate ozone within the free space. The deodorizing layer may comprise a porous filter with communicating pores owing to a three-dimensional skeleton structure.

Ozone generated by the ultraviolet-ray lamp disposed in the free space portion of the simplified deodorizing apparatus is caused to pass in contact with the deodorizing layer by the heat-generating action of the lamp as it is subject to a decomposition reaction and is diffused outside in the form of oxygen. Bad-smelling air in the outside is drawn into the free space to replace the ozone passing out through the deodorizing material as this diffusion progresses, and bad-smelling components of the air are subject to oxidation decomposition so as to be deodorized when contacted by ozone passing through the free space portion and in contact with the deodorizing layer and diffused outside. The diffusion and drawing-in operation are performed in this manner so that the air in a sealed-up space surrounding the deodorizing apparatus is circulated for a long time to effect deodorization.

BRIEF DESCRIPTION OF THE DRAWINGS

The preferred embodiments of the invention will be described in connection with the attached drawings, wherein.

DESCRIPTION OF THE PREFERRED EMBODIMENTS

Figure 1:
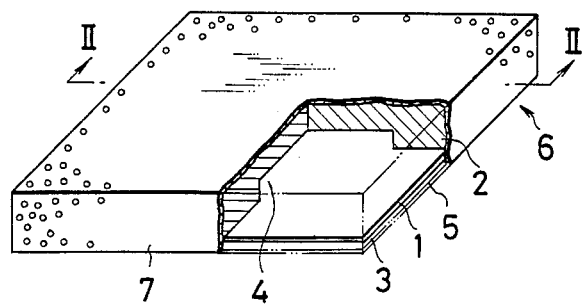
FIG. 1 is a perspective view partially broken away illustrating one embodiment of a simplified deodorizing apparatus made according to the present invention.

In the drawings, first, description will be made in detail as to embodiments belonging to a first group according to the present invention, referring to FIGS. 1 through 6. The reference numeral 1 designates electric-field energy means for generating ozone; 2, a layer of deodorizing material; 3, a gas-impermeable member; 4, an open space portion in which the electric field is created; 5, a deodorizer body; 6, a deodorizing apparatus; 7, an ozone-resistant and gas-permeable outer cover, and 8, an ozone-resistant and gas permeable inner shell.

The energy means 1 for creating the electric field for generating ozone is arranged such that linear or belt-like electrodes 1b and 1c are buried in an electrically-insulating layer 1a offset from one another in planes parallel to each other. Upon application of a high voltage from an A.C. power source 8 across the electrodes 1b and 1c through electric wires 8a, silent (corona) discharge is generated, creating an electric field in any gas in the free space portion 4 in the vicinity of the upper surface of the layer 1a which thereby generates ozone from oxygen in the gas within the space.

Figure 2:
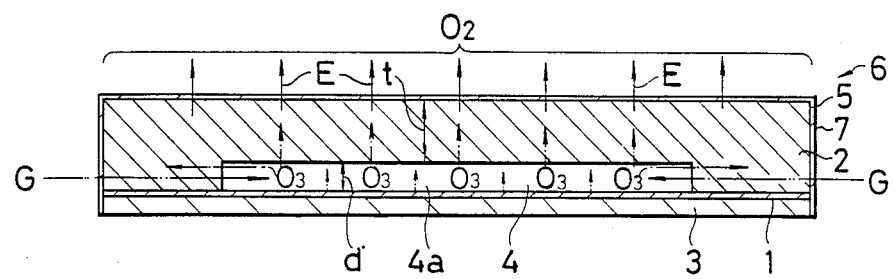
FIG. 2 is an enlarged cross-section taken on line II—II of FIG. 1.
Figure 3:
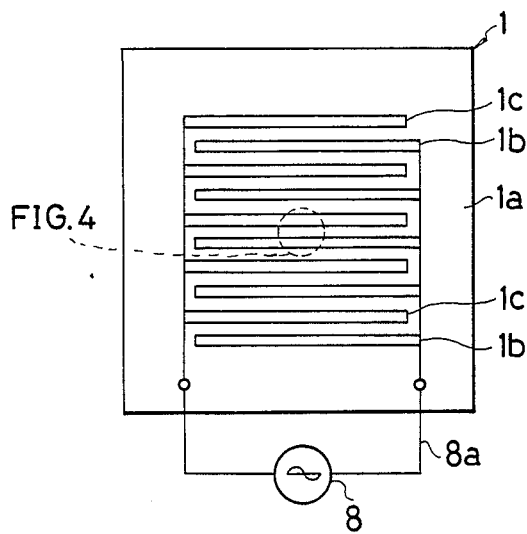
FIG. 3 is a diagrammatic plan view of the electric-field generating energy means.
Figure 4:
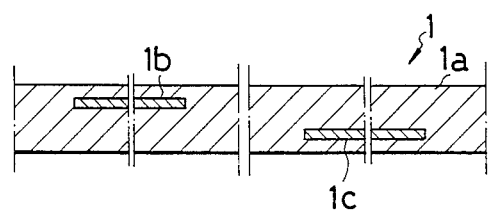
FIG. 4 is an enlarged cross section showing the portion of the energy means encircled by a broken line in FIG. 3.

The deodorizer body 5 in FIGS. 1-4 comprises a porous filter, acting as a support, and having communicating pores due to a three-dimensional skeleton structure. The deodorizer body 5 comprises the deodorizing material 2 which is prepared by applying an ozone-decomposing catalyzer, which will be described later, to the support structure. In FIGS. 1 and 2, the body also includes electrically-insulating gas-impermeable member 3 such as a ceramic plate, or the like underlying the field-generating means 1, and a foramenous shell 7 surrounding the filter structure. The deodorizer body 5 is provided with a free space portion 4 having a volume which is large enough to overlie the electrodes of the electric-field energy means 1 to generate ozone therein. That is, in the deodorizing apparatus 6 according to the present invention, the energy means 1 is disposed to create an electric field in the space portion 4 so that the electric field generates ozone therein.

Figure 5:
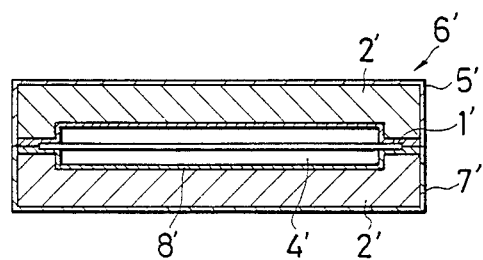
FIG. 5 is a cross section showing another embodiment of a deodorizing apparatus made according to the present invention.

The deodorizing apparatus of FIG. 2 is constituted by a layer of deodorizing material 2 and a gas-impermeable member 3 on which the electric field means 1 is arranged so as to be capable of creating an electric field to generate ozone in the free space 4. On the other hand, the deodorizing apparatus of FIG. 5 is constituted only by the deodorizing layer 2' provided with the electric field energy means 1' which is disposed in an intermediate portion of the open space portion 4' of the deodorizing layer 2'. In this embodiment, the layer of deodorizing material 2' is particulate and is confined by an outer foramenous cover 7' and an inner shell 8'. A suitable material 2' may be granules of sorbent material having a catalyzer incorporated therein by sorption. Other particulate materials may be used to provide a porous layer through which the gas may find a flow path.

The porous filter 2 provides a skeleton structure which is resistant to ozone, and may be a porous ceramic material, for example, materials sold under the trade name CERAMIC FOAM (produced by Bridgestone Corporation), or a porous metallic material, for example, material sold under the trade name CELMET (produced by Sumitomo Electric Industries Ltd.). These materials are provided with communicating pores due to a three-dimensional skeleton structure, and have capability of absorbing or adsorbing and concentrating bad-smelling components (including hydrogen sulfide, ammonia, and other components emitting a bad smell). As the catalyzer, transition metal oxide such as nickel oxide, copper oxide, or the like, precious metal such as platinum or the like, or a mixture of these materials, may be suitably applied to the porous structure.

In the simplified deodorizing apparatus 6 as illustrated in FIG. 2 according to the present invention, upon application of a high voltage (2.1–3.5 Kv) from the A.C. power source 8 across the electrodes 1b and 1c of the electric field means 1, silent (corona) discharge is created in the gas in the space 4a in the vicinity of a surface of the electrically insulating layer 1a to thereby generate ozone from oxygen in the gas as shown in the following formulae.

$$O_2 + e^- \rightarrow 2O$$

$$O + 2O_2 \rightarrow O_3 + O_2$$

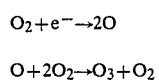

The thus-generated ozone $O_3$ is caused, by thermal and kinetic energy obtained by the discharge, to pass in a flow path through the pores of the deodorizing material 2 in intimate contact therewith as shown by one-dotted chain lines arrows and solid line arrows E while being subject to decomposition reaction described later, so as to be diffused externally of the filter body 5 as an exhaust in the form of oxygen. For example, in an arrangement such as shown in FIG. 2, the passage through the flow path in the layer 2 occurs in a defined time dependent on the size of the chamber and the applied voltage. As this diffusion progresses, the exterior bad-smelling air G is drawn into the space 4 through the pores of the deodorizing material 2 along the arrows shown by two-dotted chain lines in FIG. 2 while being partly subject to absorption or adsorption and concentration of bad-smelling components thereof. Some of the oxygen in the air in the space 4 is converted to ozone, and the remaining gas is thereafter exhausted as deodorized air after being subject to oxidation decomposition as will be described later. Thus, exhaust and drawing-in are performed gently to thereby circulate air in a sealed-up space surrounding the deodorizing apparatus 6 so deodorization progresses slowly as a whole.

The foregoing ozone decomposition reaction progresses through the following processes, so that ozone is decomposed into oxygen to be made harmless before the ozone reaches the outside surface of the deodorizing material 2. That is, (I) self-decomposition reaction ($2O_3 \rightarrow 3O_2$) is performed in the space portion 4, and (II) ozone absorbed and concentrated by the deodorizing material 2 is decomposed ($O_3 + M \rightarrow O_2 + O + M$, where M represents a catalyzer) by an ozone decomposing catalyzer. Further, the ozone in the space portion 4 is relatively stable because the half-life thereof is within a range from several hours to approximately ten hours and therefore the greater part of ozone is decomposed in the process (II). The quantity of ozone generated depends on the voltage applied, the volume of the free space portion, and so on. On the other hand, the quantity of ozone decomposition depends on the thickness of the deodorizing layer 2 and thus the length of the flow path for ozone, and the quantity of the catalyzer carried by the material. Therefore, by suitably adjusting those factors, it is possible to form an atmosphere having high concentration of ozone in the space portion 4 without allowing ozone to be exhausted from the deodorizing apparatus 6.

The foregoing oxidation decomposition and deodorization of bad-smelling components is effected through the following process. That is, (I) the bad-smelling components are subject to vapor phase oxidation decomposition with ozone in the free space portion 4; (II) the bad-smelling components are subject to oxidation decomposition by ozone or the catalyzer after being absorbed or adsorbed by the deodorizing material 2; (III) the bad-smelling components are decomposed by ozone entrained by sorption in the deodorizing material or by an activator (nascent oxygen O) generated from ozone which is decomposed after sorption. The deodorization is effected mainly through the processes (II) and (III). That is, the bad-smelling components, which are partially absorbed or adsorbed and concentrated by the deodorizing layer 2 as the incoming air passes in contact with the layer, are decomposed through the reaction process (II). Further, under the conditions such that the oxidation decomposition for deodorizing bad-smelling components in bad-smelling air G have progressed to make the quantity of bad-smelling components zero, ozone generated from the electric field means 1 is repeatedly decomposed by the same ozone decomposing reaction as the foregoing one, and is diffused externally in the harmless state. Porous material provides maximum contact between the material and the gaseous material in the flow path through the material, but ozone-decomposing materials in other configurations may provide a flow path to supply the desired contact between the material and the gaseous medium in the flow path.

Figure 6:
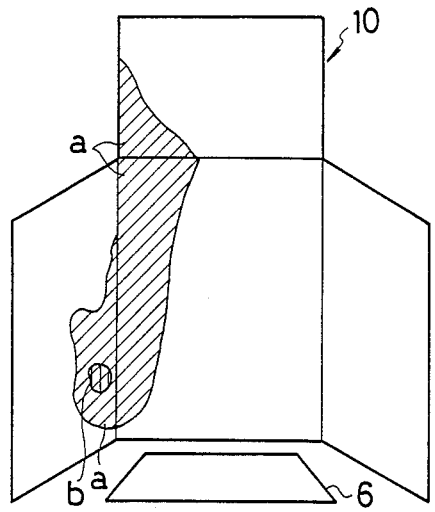
FIGS. 6 through 8 are schematic views of a test chamber used for explaining the process of generating and diffusing ozone.
Figure 7:
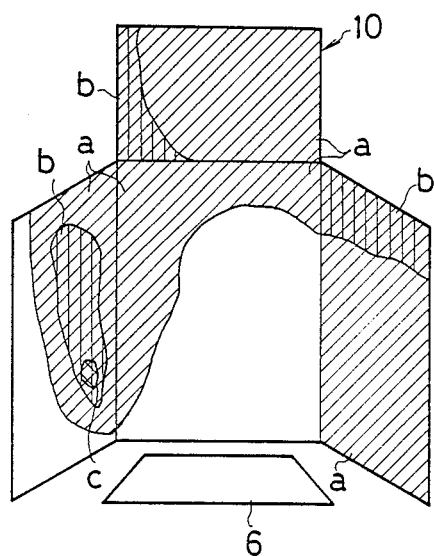
Figure 8:
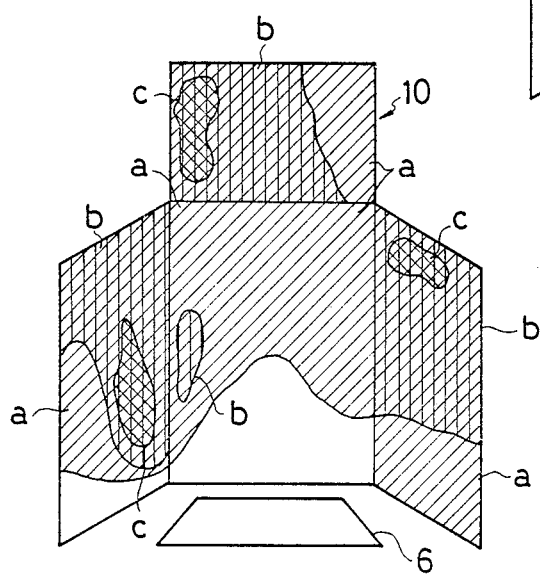
Figure 9:
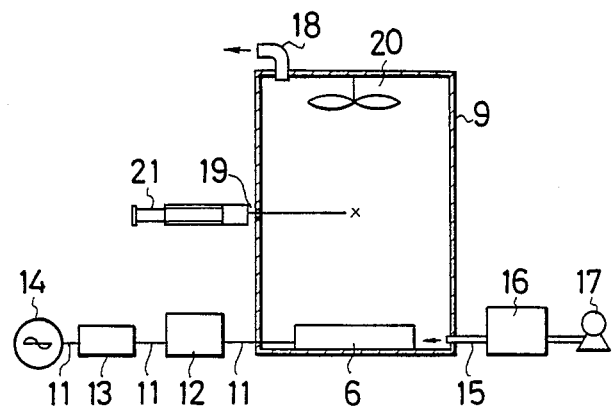
FIG. 9 is a schematic view showing an apparatus for testing deodorizing apparatus according to the present invention.

FIGS. 6 through 9 are views showing experimental test apparatus for proving the fact that air in a sealed-up space surrounding the deodorizing apparatus 6 is deodorized as described above. The deodorizing apparatus 6 was set on a bottom wall surface of a sealed-up box 9 having a volume of 15.5 liters, as shown in FIG. 9, and potassium iodate-starch paper 10 was applied to cover the three side wall surfaces and the whole top wall surface. Next, a high voltage was applied to the electric-field generating means 1 to generate ozone. The paper 10 began to change in color to indicate it was touched by ozone, and the process of generation and diffusion of ozone was indicated. The results of this experiment are shown in FIGS. 6, 7 and 8, in which degrees of discoloration when 10, 30, and 60 minutes elapsed after the application of voltage are classified into three stages of a, b, and c (a b c). That is, generated ozone rises along the left side wall surface in FIG. 6 up to come into contact with the top wall surface in spite of the fact that the specific gravity of ozone is larger than air. Then, the ozone changes its direction to come to the right side wall surface and then comes down along the right side wall surface to the bottom wall surface. Thus, the deodorizing apparatus 6 according to the present invention causes such circulation of ozone as described above, and the circulation can be repeatedly performed without requiring any separate means for circulation.

Figure 10:
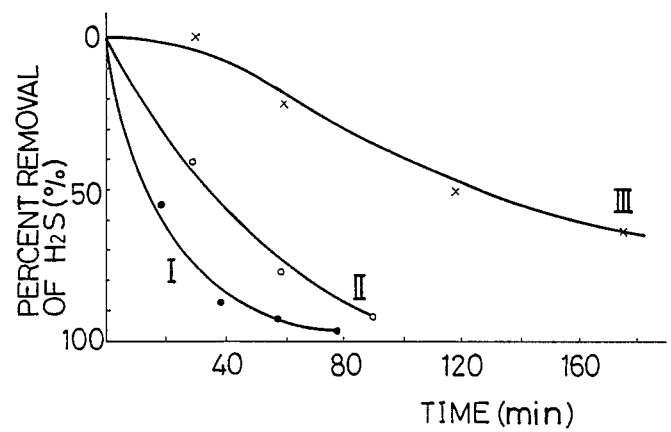
FIG. 10 is a graph for explaining the deodorizing tests.

Referring now to FIG. 9, a deodorizing effect resulting from use of the deodorizing apparatus 6 according to the present invention will be described. The deodorizing apparatus 6, in which a thickness t of the deodorizing layer 2 is selected to be 10 mm and the distance d representing the free space between the electric-field energy means 1 and the deodorizing layer 2 is selected to be 5 mm, was set in the sealed-up box 9 used in the foregoing experiment. The electric-field energy means 1 was connected to a transformer 12, a variable transformer 13, and a power source 14, in this order, through electric wires 11. The reference numeral 15 designates a pipe; 16, a drier; 17, a blower; 18, a discharge hole; 19, a measuring hole; and 20, a stirring fan, for example an axial fan. After humidity in the box 9 was made constant by the drier 16, the box 9 was filled with high concentration hydrogen sulfide by using a syringe 21, and the gaseous contents inside of the box 9 were stirred by the blade 20 to make the concentration of hydrogen sulfide inside the box 9 uniform (30–40 ppm). Upon application of a voltage of 3.5 Kv to the electric-field energy means 1, the percent removal of hydrogen sulfide increased as time elapsed as shown by curve I in FIG. 10. In FIG. 10, curve II shows the result under the same conditions in the case of the curve I except no voltage was applied to the electric-field energy means 1, and curve III, on the contrary, shows the result under the same condition in the case of the curve I except no catalyzer was applied to the porous filter layer 2 and no voltage was applied to the electric-field energy means 1. As to the curves III and II, it is considered that the percent removal of hydrogen sulfide is increased after a time period because the hydrogen sulfide is absorbed and concentrated in the porous filter and because the hydrogen sulfide is reacted with a catalyzer to be decomposed in addition to the sorption and concentration in the porous filter, respectively. Under the conditions of the curves II and III, if a voltage is applied to the electric-field generating means 1 to generate ozone, decomposition of hydrogen sulfide due to ozone and an activator is increased as described above, so that the percent removal of hydrogen sulfide is increased as shown by the curve I.

The deodorizing apparatus 6 according to the present invention is free from danger because no ozone flows out of the deodorizing apparatus 6, and the safety can be proved by the following experiment and Tables showing the results. That is, the deodorizing apparatus 6 was set in the sealed-up box 9 used in the foregoing experiments. In this experiment, concentration (ppm) of ozone flowing out of the deodorizing apparatus 6 was measured while varying the thickness t of the deodorizing layer 2, the applied voltage Kv, and the distance d between the electric field means 1 and the deodorizing layer 2. In the measurement, a gas detection pipe for ozone was used and the concentration of ozone was measured from the measuring hole 19. The following Tables show the results of measurement.

TABLE 1

| | (thickness t of deodorizing layer = 10 mm) | | | | |
|---|---|---|---|---|---|
| | Applied voltage: | | | | |
| Distance d | 2.10 KV | 2.45 KV | 2.80 KV | 3.15 KV | 3.50 KV |
| 5 mm | 0 | 0 | 0 | 0 | 0 |
| 10 mm | 0 | 0 | 0.07 ppm | 1.0 ppm | — |
| 18 mm | 0 | 0 | 1.10 ppm | 1.8 ppm | — |

TABLE 2

| | (thickness t of deodorizing layer = 20 mm) | | |
|---|---|---|---|
| | Applied voltage: | | |
| Distance d | 2.80 KV | 3.15 KV | 3.50 KV |
| 10 mm | 0 | 0 | 0 |
| 18 mm | 0 | 0 | 0.05 ppm |

Each of numerical values in Tables is a measurement value of the concentration (ppm) of ozone in the box 9 when 60 minutes have elapsed after application of voltage. That is, in order to prevent ozone from flowing outside the deodorizing apparatus, the foregoing various elements may be determined on the basis of proper values in Tables. Furthermore, the concentration of ozone was 5.1 ppm when measured after a lapse of 30 minutes in the deodorizing apparatus when a porous filter having a thickness of 10 mm with no catalyzer applied thereto was used in place of the deodorizing material where the distance (d) between the porous filter and the electric field means was selected to be 5 mm, and a voltage of 2.1 Kv was applied to the electric field means.

Referring to FIGS. 11 through 18, description will be made in detail as to embodiments belonging to a second group according to the present invention. In the drawings of these embodiments, the reference numeral 31 designates an ultraviolet-ray lamp; 32, a deodorizing material; 33, a gas-impermeable member underlying the lamp in FIGS. 11-14 and at one end in FIG. 15; 34, a free space portion; 35, a deodorizer body; 36, a deodorizing apparatus; 37, an ozone-resistant and gas-permeable outer cover; and 38, an ozone-resistant and gas-permeable inner shell.

The ultraviolet-ray lamp 31 for generating ozone radiates light having wavelengths not larger than 200 ni, and particularly strongly radiates light having a wavelength of 185 nm. Oxygen in the open space portion 34 absorbs light of such wavelengths, enabling the oxygen to be changed into ozone. The deodorizer body 35 includes a porous filter layer comprising a block of deodorizing material 32, as a support, having communicating pores due to a three-dimensional skeleton structure. The deodorizer body 35 may consist of the deodorizing layer 32 having applied thereto an ozone-decomposing catalyzer alone as in FIGS. 16-18, which will be described later, or may consist of the deodorizing layer 32 and the electrically insulating gas-impermeable member 33 such as a ceramic plate, or the like as in FIGS. 11-14. The deodorizer body 35 is provided with a free space portion 34 having a volume which is large enough to accommodate the ultraviolet-ray lamp 31, or at least the luminous tube portion 31a of the lamp 31, therein to generate ozone in the free space 34. That is, in the deodorizing apparatus 36 according to the present invention, at least the luminous tube portion 31a of the ultraviolet-ray lamp 31 is accommodated in the free space portion 34 of the deodorizer body 35 so that ozone can be generated in the free space portion 34 and the free space portion 34 is closed so as to integrate the luminous tube portion 31a within the deodorizer body 35.

Figure 11:
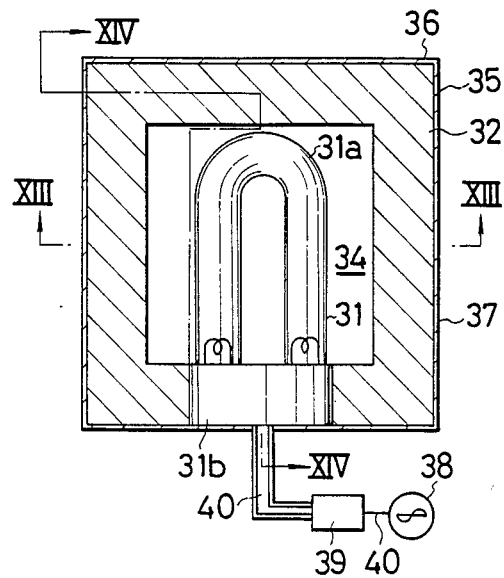
FIG. 11 is a transverse cross-section showing a further embodiment of a simplified deodorizing apparatus made according to the present invention.
Figure 15:
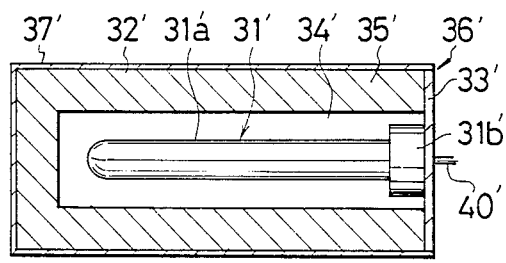
FIGS. 15 through 18 are views showing still further embodiments of simplified deodorizing apparatus made according to the present invention, FIGS. 15 and 18 being cross sections of different apparatus, FIG. 16 being a side view partly in section of another embodiment and FIG. 17 being a cross section taken on XVII—XVII line in FIG. 16.

The deodorizing apparatus of FIG. 11 is constituted by the deodorizing layer 32 and the gas-impermeable member 33. The luminous tube portion 31a of the lamp 31 is provided in the free space portion 34 so that ozone can be generated therein, and a socket portion 31b of the lamp 31 is secured within the deodorizing layer 32. The deodorizing apparatus of FIG. 15 is constituted by a deodorizer body 35' similar to that of FIG. 11, and corresponding parts of the apparatus 36' have been designated with primed reference characters. In this embodiment, however, the entire lamp 31' is disposed in the space portion 34', and the gas-impermeable member 33' is positioned at the end to support the socket portion 31b'.

Figure 16:
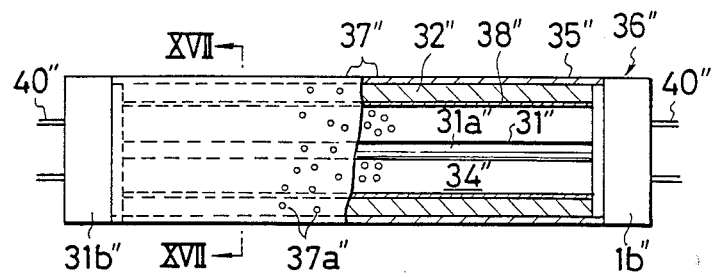
Figure 18:
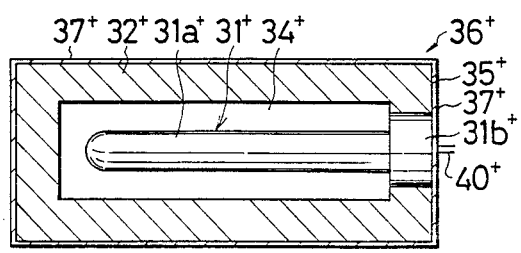
Figure 17:
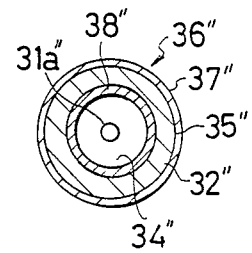

In the embodiment shown in FIGS. 16 and 17, corresponding parts of the apparatus 36" have been designated with double-primed reference characters. The inner shell 38" and the outer cover 37" are of hollow cylindrical form so that the layer 32" is a cylindrical annulus. The lamp 31" is a fluorescent tube. In the embodiment of FIG. 18, the corresponding parts of the apparatus 36+ have been designated with a crossed prime. In this embodiment the body 36+ is similar to the body 36', but without the ceramic plate 33'. In each case, the deodorizer body 35 is constituted by the deodorizing layer 32, and the luminous tube portion 31a is disposed in the free space portion 34.

As the layer 32 one may use a porous ceramic structure, for example, materials sold under the trade name CERAMIC FOAM (produced by Bridgestone Corporation), or a porous metallic material, for example material sold under the trade name CELMET (produced by Sumitomo Electric Industries Ltd.), or a particulate ozone-decomposing material, for example as shown in FIGS. 16 and 17 confined between the foramenous outer cover 37" and the foramenous inner shell 38". The porous materials are provided with communicating pores which provide a flow path for the gaseous medium due to a three-dimensional skeleton structure. The particulate material provides a flow path between the particles. All of the materials have capability of entraining by sorption and concentrating bad-smelling components (including hydrogen sulfide, ammonia, and other components emitting a bad smell) as the foul air passes in contact with the material. As the catalyzer, transition metal oxide such as nickel oxide, copper oxide, or the like, precious metal such as platinum or the like, or a mixture of these materials, may be suitably used. The reference numeral 37a designates pores or perforations.

Figure 12:
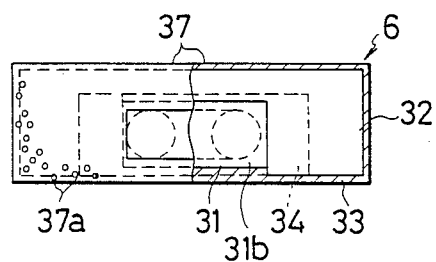
FIG. 12 is an end view partly broken away showing the same embodiment.
Figure 13:
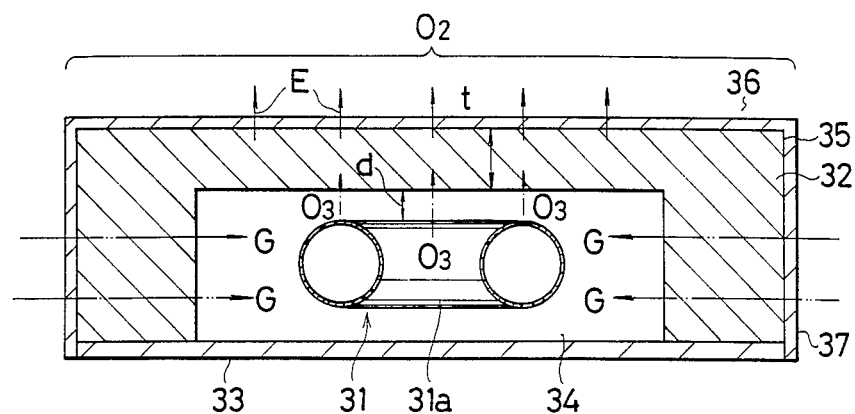
FIG. 13 is an enlarged cross-section taken on line XIII—XIII in FIG. 11.
Figure 14:
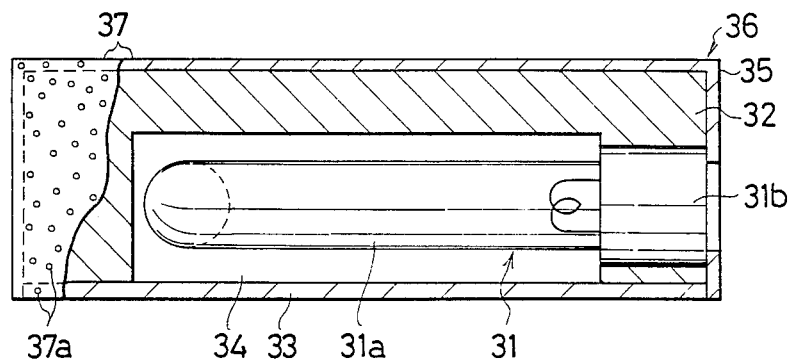
FIG. 14 is an enlarged cross-section taken on line XIV—XIV in FIG. 11.

In the simplified deodorizing apparatus 36 according to the present invention shown in FIGS. 11 to 13, when applied with a voltage from an A.C. power source 38 through a voltage regulator 39 and electric wires 40, the ultraviolet lamp 31 for generating ozone radiates light of wavelengths not larger than 200 nm, and mainly strongly radiates light of a wavelength of 185 nm. Oxygen in the space portion 34 absorbs the light of the wavelengths, so that ozone is generated on the basis of the following formulae.

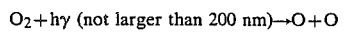

$O_2 + h\gamma$ (not larger than 200 nm) $\rightarrow O + O$

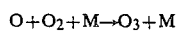

$O + O_2 + M \rightarrow O_3 + M$ (M represents substance, such as $O_2$, $N_2$, etc.).

The thus generated ozone $O_3$ is caused, by thermal energy generated by the ultraviolet-ray lamp 31, to pass in contact with the deodorizing layer 32 in the flow paths as shown by one-dotted chain lines arrows and solid line arrows E while being subject to decomposition reaction described later. The flow paths through the apparatus provide sufficiently small flow resistance to permit the thermal and kinetic energy created to cause the desired flow. After decomposition, the flow is diffused externally in the form of oxygen, for example, in such an arrangement as shown in FIG. 13 and in a predetermined time period. As this diffusion is effected, the exterior foul air G is passed through the pores of the deodorizing material 32 along the arrows shown by two-dotted chain lines G in FIG. 13 while being partly subject to sorption and concentration of bad-smelling components thereof, then drawn into the free space portion 34, and thereafter diffused externally from the body 32 as deodorized air after being subject to oxidation decomposition as will be described later. Thus, diffusion and taking-in are gently performed to thereby circulate air in the space surrounding the deodorizing apparatus 36 so as to effect deodorization slowly as a whole.

The foregoing ozone decomposition reaction progresses through the following processes, so that ozone is decomposed into oxygen within the body to be made harmless before the ozone reaches the outer surface of the body of the deodorizing layer 32. That is, (I) self-decomposition reaction ($2O_3 \rightarrow 3O_2$) is performed in the space portion 34; and (II) ozone is absorbed or adsorbed and concentration by the deodorizing material 32 and is decomposed by an ozone decomposing catalyzer:

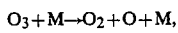
$O_3 + M \rightarrow O_2 + O + M,$ where M represents a catalyzer. Further, the ozone in the space portion 34 is relatively stable because the half-life thereof is within a range from several hours to approximately ten hours and therefore the greater part of ozone is decomposed in the process (II).

The quantity of ozone generated depends on the energy distribution and intensity of illumination of the ultraviolet-ray lamp, and other factors, and on the other hand the quantity of ozone decomposition depends on the thickness of the deodorizing layer 32, or the length of the flow path through the layer, and the quantity of the catalyzer carried in the material. Therefore, by suitably adjusting those factors, it is possible to form an atmosphere of ozone having high concentration in the free space portion 34 without allowing ozone to come out of the deodorizing apparatus 36.

The foregoing oxidation decomposition and deodorization of bad-smelling components is effected through the following process. That is, (I) the bad-smelling components are subject to vapor phase oxidation decomposition with ozone in the free space portion; (II) the bad-smelling components are subject to oxidation decomposition by ozone or the catalyzer after being incorporated by sorption in the deodorizing layer; (III) the bad-smelling components are decomposed by ozone incorporated in the deodorizing layer or by an activator (nascent oxygen O) generated from ozone which is decomposed after being incorporated. The deodorization is progressed mainly through the processes (II) and (III). That is, the bad-smelling components which are partially incorporated by sorption and concentrated by the deodorizing layer are decomposed through the reaction process (II). Further, under the condition that the oxidation decomposition for deodorizing bad-smelling components in foul air G has progressed to make the quantity of bad-smelling components zero, ozone generated by the ultraviolet-ray lamp 31 is repeatedly decomposed by the same reaction as the foregoing decomposition reaction of ozone and diffused externally in the harmless state.

Figure 19:
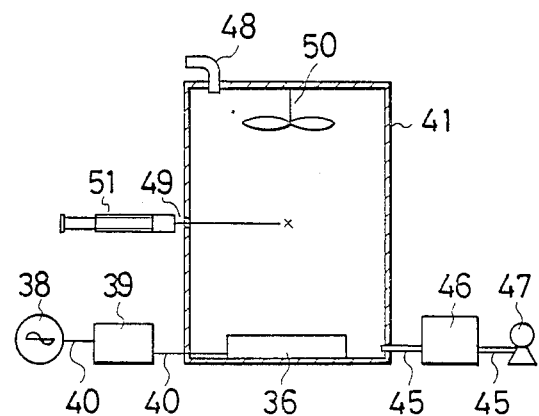
FIG. 19 is a view of test apparatus for testing the simplified deodorizing apparatus according to the present invention.
Figure 20:
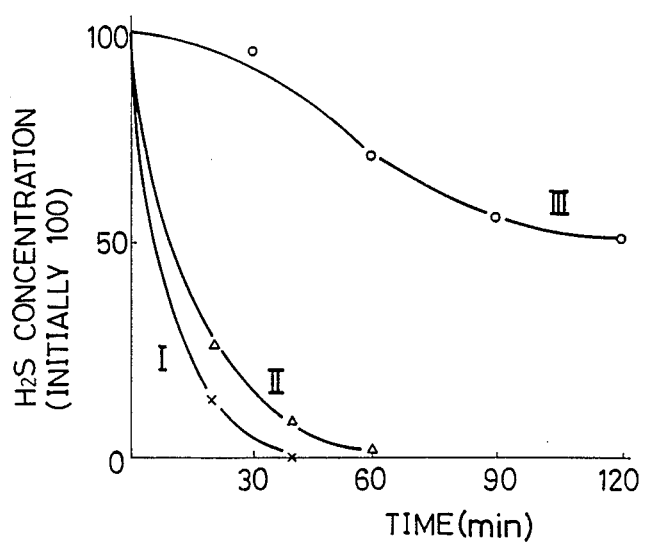
FIGS. 20 and 21 are graphs showing the deodorizing effect achieved by the deodorizing apparatus in tests performed in the apparatus of FIG. 19.

Referring now to FIGS. 19 and 20, a deodorizing effect owing to the deodorizing apparatus 36 according to the present invention will be described. The deodorizing apparatus 36, in which the thickness t of the porous deodorizing layer 32 is selected to be 10 mm and the distance d in the space 34 between the ultraviolet-ray lamp 31a and the inner surface of the deodorizing layer 32 is selected to be 5 mm, was set in a sealed-up box 49 having an interior volume of 15.5 liters. The deodorizing apparatus 36 was connected to the power source 38 through the electric wires 40 and the voltage regulator 39. The reference numeral 45 designates a pipe; 46, a drier; 47, a blower; 48, a discharge hole; 49, a measuring hole; and 50, a stirring fan. After the humidity in the box 41 was made constant by the drier 46, the box 41 was filled with high concentration hydrogen sulfide by using a syringe 51, and the inside of the box 41 was stirred by the fan 50 to make the concentration of hydrogen sulfide inside the box 41 uniform (30–40 ppm). Change in concentration of hydrogen sulfide inside the box 41 as time elapsed was measured by using a gas sensing tube for hydrogen sulfide. FIG. 20 shows the results of measurement. In FIG. 20, the curve I shows the result when the experiment was performed with the ultraviolet-ray lamp 31 kept on (Experiment I), the curve II shows the result when the experiment was performed with the ultraviolet-ray lamp 31 kept off (Experiment II), and the curve III shows the result when the experiment was performed by using a standard (non-ozone-decomposing) porous filter in place of the deodorizing layer 32 with the ultraviolet-ray lamp 31 kept off (Experiment III). Other conditions were the same as those described above. In the example of Experiment III, although decomposition of hydrogen sulfide by ozone and catalyzer cannot be expected, it is considered that the reduction in concentration of hydrogen sulfide mainly depends on sorption and concentration of hydrogen sulfide by the porous filter or sorption of hydrogen sulfide into the exposed surfaces in the test apparatus. In the example of Experiment II, on the other hand, it is considered that a reaction between the hydrogen sulfide and the catalyzer occurred in addition to the foregoing sorption and concentration so that the concentration of hydrogen sulfide was exceedingly reduced in comparison with the result of Experiment III. When ozone was generated with the lamp 31 kept on under the condition of Experiment II, the concentration of hydrogen sulfide was further reduced as shown by the curve I. That is, it is understood that ozone effectively assists removal of hydrogen sulfide.

Figure 21:
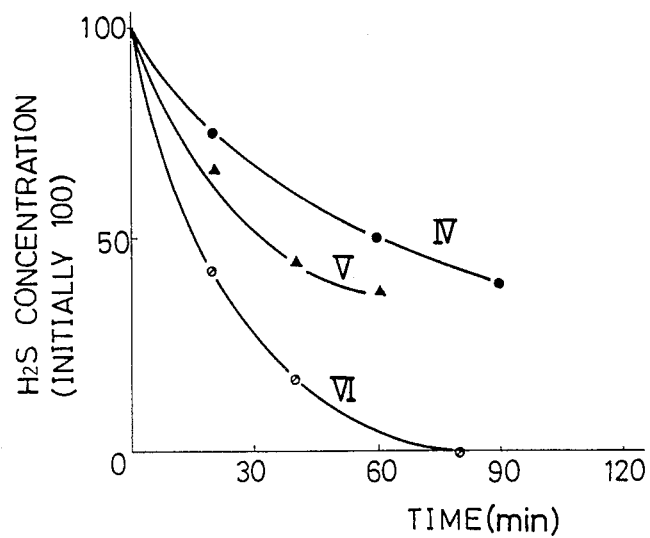

As seen from the following experiments, and FIG. 21 showing the results thereof, owing to the deodorizing apparatus 36 according to the present invention, ozone has a capability of reactivating a deteriorated catalyzer to increase the deodorizing effect of the catalyzer. That is, the curve IV shows the result of the case where the deodorizing apparatus 36 was left for 60 minutes in an atmosphere of hydrogen sulfide having high concentration (0.1%) in a separately prepared vessel, was taken out of the vessel, and then was put in the box 41 in the same conditions as those in the foregoing experiments so as to perform the experiment with the lamp 31 kept off (Experiment IV). The curve V shows the result in the case where the deodorizing apparatus 36 immediately after the Experiment IV was left for 30 minutes in an atmosphere of ozone in a further separately prepared vessel, was taken out of the further vessel, and was put in the box 41 under the same conditions as those in the foregoing experiment so that the experiment was performed with the lamp 31 kept off similarly (Experiment V). The curve VI shows the result of the case where the experiment was performed under the condition that ozone was generated by turning on the lamp 31 of the deodorizing apparatus 36 after the Experiment V (Experiment VI). As apparent from the results, the performance of removing hydrogen sulfide is exceedingly slow in the curve IV compared with that in the curve II obtained under the same conditions as those in the curve IV. It is conjectured that the catalyzer and hydrogen sulfide are reacted with each other to generate sulfide to thereby deteriorate reactivity of the catalyzer. The performance for removing generated sulfide by the deodorizer body 36 having the deteriorated catalyzer is reactivated in the atmosphere of ozone as shown by the curve V, and the performance was further improved in Experiment VI performed in the state where ozone was generated. Thus, it is understood that ozone reactivates the catalyzer deteriorated in performance by hydrogen sulfide (that is, by decomposition of generated sulfide) to thereby increase the deodorizing effect of the catalyzer.

The deodorizing apparatus 36 according to the present invention is free from danger because no ozone ever flows out of the deodorizing apparatus 36, and the safety can be proved by the following experiments and Tables. That is, the deodorizing apparatus 36 was set in the sealed-up box 41 used in the foregoing experiments. In this experiment, the concentration of ozone flowing out of the deodorizing apparatus 36 after the lamp was turned on was measured as time elapses, under the conditions that the thickness t of the deodorizing layer 32 (and thus the length of the flow path) was made constant (t=10 mm) and the distance d between the lamp 31 and the deodorizing material 32 was changed from 5 mm to 13 mm. In the measurement, a gas detection tube for ozone was used and the measurement was performed through the measuring hole 49. The following Tables show the results of measurement. Further, the result of measurement in the case where a standard porous filter having a thickness of 10 mm was used in place of the deodorizing layer 32 is shown in Table 5 as a comparative example.

TABLE 3

| | (distance d = 5 mm) | | | |
|---|---|---|---|---|
| Time | 0 min | 30 min | 60 min | 90 min |
| Concentration of O$_3$ | 0 ppm | 0 ppm | 0 ppm | 0 ppm |

TABLE 4

| | (distance d = 13 mm) | | | |
|---|---|---|---|---|
| Time | 0 min | 30 min | 60 min | 90 min |
| Concentration of O$_3$ | 0 ppm | 0 ppm | 0 ppm | 0 ppm |

TABLE 5

| | (distance d = 5 mm) | |
|---|---|---|
| Time | 0 min | 20 min |
| Concentration of O$_3$ | 0 ppm | 12 ppm |

As seen from numerical values in Tables, ozone did not flow out at all with apparatus of the present invention, and therefore it is possible to confirm the safety of the deodorizing apparatus 36. In Table 5, where the deodorizing material is replaced by a conventional filter material, ozone having concentration of 12 ppm flowed out. Ozone concentration of this numerical value becomes harmful as time elapses.

According to the present invention, the deodorizing apparatus can be easily reduced in size and simplified in arrangement and therefore it is possible to enlarge the field of utilization of the deodorizing apparatus so as to be applicable to general home use. Thus, remarkable effects are achieved by deodorizing apparatus made in accordance with the invention, as set forth in the following claims.

We claim:

1. A deodorizing apparatus comprising energy means for creating an electric field for generating ozone and imparting thermal and kinetic energy to the ozone, and a deodorizer body, said deodorizer body comprising a layer operating for decomposing ozone, said deodorizer body having an interior free space portion, said energy means being mounted adjacent said free space portion such that it creates an electric field within said space to generate ozone therein, said layer being constructed and positioned with respect to said free space portion to require ozone generated in said free space portion to flow in a path in contact with said layer.

2. A deodorizing apparatus according to claim 1 in which said ozone-decomposing layer has a composition and is dimensioned and arranged to retain by sorption and to concentrate bad-smelling components of air flowing therethrough.

3. A deodorizing apparatus according to claim 2 wherein said layer is formed as a porous filter body having a three-dimensional skeleton structure forming communicating pores providing a flow path therethrough for ozone from said free space toward the space surrounding said body.

4. A deodorizing apparatus according to claim 1 wherein said ozone-decomposing layer incorporates a catalyzer and provides a flow path sufficiently long to effect decomposition of the ozone under the influence of said catalyzer before substantially any ozone can pass out of the body.

5. A deodorizing apparatus according to claim 1 including an electrically-insulating gas impermeable member at one side of said free space to restrict the flow of ozone in the direction of said member.

6. A deodorizing apparatus according to claim 1 including a foramenous casing surrounding said layer.

7. A deodorizing apparatus according to claim 6 wherein said layer comprises particulate material confined within said casing.

8. A deodorizing apparatus comprising an ultraviolet-ray lamp for radiating ultraviolet rays of short wavelength to generate ozone and imparting thermal and kinetic energy to the ozone, and a deodorizer body, said deodorizer body comprising a layer operative for decomposing ozone, said deodorizer body having an interior free space portion positioned for accommodating said ultraviolet rays radiated by said ultraviolet-ray lamp so that the lamp can generate ozone in said space portion, said layer being constructed and positioned with respect to said free space portion to cause the thermal and kinetic energy in the ozone generated in said free space portion to effect flow in said path in contact with said layer.

9. A deodorizing according to claim 8, in which said layer has a composition and is dimensioned and arranged so as to retain by sorption and to concentrate bad-smelling components of air flowing in contact therewith.

10. A deodorizing apparatus according to claim 8 wherein said filter layer incorporates a catalyzer and said flow path is sufficiently long to effect decomposition of the ozone under the influence of said catalyzer before substantially any ozone can pass out of the body.

11. A deodorizing apparatus according to claim 8 wherein said layer comprises a deodorizing material formed as a porous filter having a three-dimensional skeleton structure forming communicating pores providing said flow path therethrough for ozone from said free space toward the space surrounding said body.

12. A deodorizing apparatus according to claim 8 including a foramenous casing surrounding said layer.

13. A deodorizing apparatus according to claim 12 wherein said layer comprises particulate material confined within said casing.

14. A method of deodorizing bad-smelling air comprising the steps of:
providing a deodorizer body having an ozone-decomposing layer and an interior free space;
supplying energy to said free space so as to generate ozone having thermal and kinetic energy in said free space, said thermal and kinetic energy being sufficient to cause said ozone to flow out of said free space in contact with said layer and to draw into said free space and in contact with said layer ambient air surrounding said body; and
providing a sufficiently long flow path for said ozone in said body to effect decomposition of substantially all of said ozone before substantially any ozone leaves the body, said decomposition of ozone being effective to deodorize by oxidation any bad-smelling components of the drawn-in air.

15. A method according to claim 14 wherein the flow of decomposed ozone leaving the body effects gentle circulation of air in the space surrounding said apparatus and into said free space within said body.

* * * * *